US00PP33163P2

(12) United States Plant Patent
Snijder

(10) Patent No.: US PP33,163 P2
(45) Date of Patent: Jun. 15, 2021

(54) ***PELARGONIUM* PLANT NAMED 'PEQZ0077'**

(50) Latin Name: ***Pelargonium* interspecific**
Varietal Denomination: PEQZ0077

(71) Applicant: SYNGENTA CROP PROTECTION AG, Basel (CH)

(72) Inventor: Ronald Christiaan Snijder, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/912,731

(22) Filed: Jun. 26, 2020

(51) Int. Cl.
*A01H 5/02* (2018.01)
*A01H 6/42* (2018.01)

(52) U.S. Cl.
USPC ..... Plt./324
CPC ..... *A01H 6/425* (2018.05); *A01H 5/02* (2013.01)

(58) Field of Classification Search
USPC ..... Plt./324
CPC ..... A01H 6/428
See application file for complete search history.

*Primary Examiner* — Anne Marie Grunberg
(74) *Attorney, Agent, or Firm* — Dale Skalla

(57) ABSTRACT

A new *Pelargonium* plant named 'PEQZ0077' particularly distinguished by orange-red colored inflorescences with semi-double florets, held above dark green foliage, on a vigorous mounding plant.

1 Drawing Sheet

Latin name of the genus and species of the plant claimed: *Pelargonium* interspecific.

Varietal denomination: 'PEQZ0077'.

BACKGROUND OF THE NEW PLANT

The present invention comprises a new *Pelargonium*, botanically known as *Pelargonium* interspecific, and hereinafter referred to by the variety name 'PEQZ0077'.

'PEQZ0077' is a product of a planned breeding program. The new cultivar 'PEQZ0077' has orange-red colored inflorescences with semi-double florets, held above dark green foliage, on a vigorous mounding plant.

'PEQZ0077' originates from a hybridization in a controlled breeding program made in July 2015, in a greenhouse in Enkhuizen, The Netherlands. The female parent was an unpatented plant of *Pelargonium* x *hortorum* parentage identified as 'PEZ-AZ3272-07' with darker colored and larger florets and a larger plant habit when compared to 'PEQZ0077'.

The male parent of 'PEQZ0077' was an unpatented, proprietary plant of *Pelargonium* x interspecific parentage, identified as '11063-1' with lighter green foliage and orange-red, more single florets when compared to 'PEQZ0077'. The resultant seed was sown in December 2013.

'PEQZ0077' was selected as one flowering plant within the progeny of the stated cross in May 2014 in a greenhouse in Enkhuizen, The Netherlands.

The first act of asexual reproduction of 'PEQZ0077' was accomplished when vegetative cuttings were propagated from the initial selection in June 2014 in a greenhouse in Enkhuizen, The Netherlands.

BRIEF SUMMARY OF INVENTION

Horticultural examination of plants grown from cuttings of the plant initiated in May 2014 in Enkhuizen, The Netherlands and continuing thereafter, has demonstrated that the combination of characteristics as herein disclosed for 'PEQZ0077' are firmly fixed and are retained through successive generations of asexual reproduction.

'PEQZ0077' has not been observed under all possible environmental conditions. The phenotype may vary significantly with variations in environment such as temperature, light intensity, and day length.

A Plant Breeder's Right for this cultivar has not yet been applied for. 'PEQZ0077' has not been made publicly available prior to the effective filing date of this application, notwithstanding any disclosure that may have been made less than one year prior to the effective filing date of this application by the inventor or another who obtained 'PEQZ0077' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0077' with colors being as true as possible with an illustration of this type.

Figure 1:
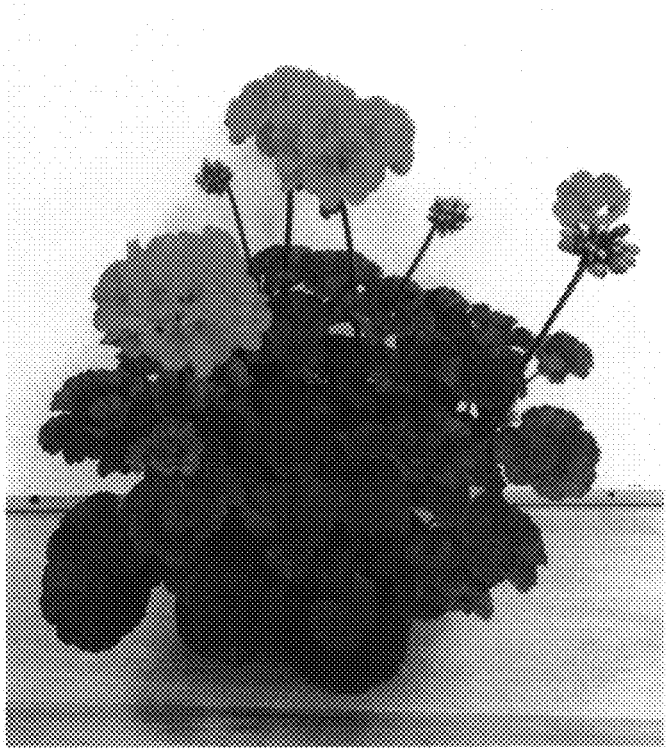
Figure 2:
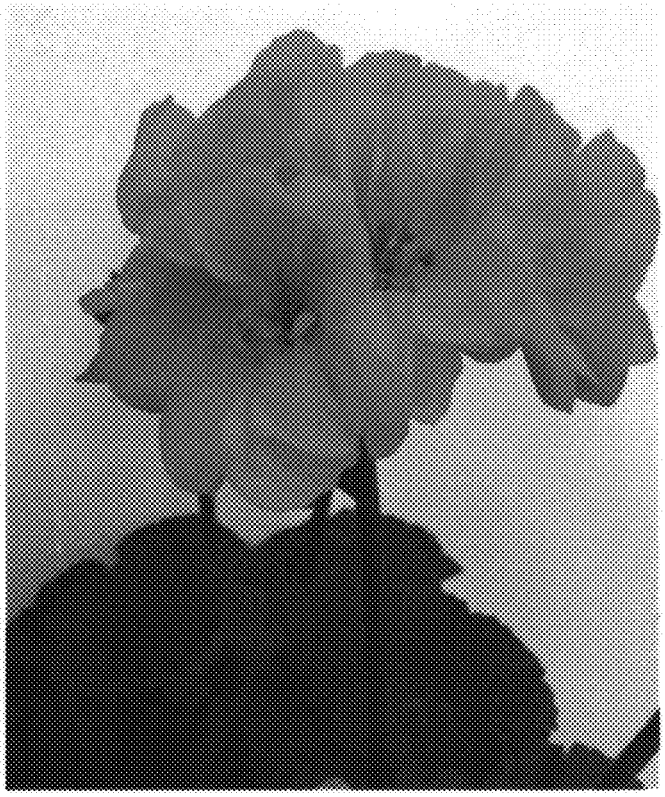

The photographic drawings show in FIG. 1, 1 flowering plant of the new variety and in FIG. 2, a close-up of an inflorescence.

DETAILED BOTANICAL DESCRIPTION

The plant descriptions and measurements were taken in Enkhuizen, The Netherlands in early June 2020 under natural light. These plants were approximately 16 weeks old and were grown in a 12 cm pots, in a greenhouse trial. The plants shown in the photographs were about 16 weeks old growing in a 12 cm pot in a greenhouse. The photographs were taken in June 2020.

Color references are made to The Royal Horticultural Society Colour Chart (R.H.S.) 2001.

TABLE 1

DIFFERENCES BETWEEN THE NEW VARIETY 'PEQZ0077' AND A MOST SIMILAR VARIETY

| | 'PEQZ0077' | 'Fisorangtan'(U.S. Plant Pat. No. 16,891) |
|---|---|---|
| Pollen color: | RHS 173B (greyed-orange) | RHS 28A (yellow-orange) |
| Peduncle color: | RHS 143C, coloring with anthocyanins towards close to RHS 181A | Between RHS 143C (light-green) and RHS 143B (light-green) |
| Stigma color: | Close to RHS 53A (dark red) | RHS 43C (salmon-pink) |

Plant:

*Form, growth and habit.*—Upright, outwardly spreading and rounded growth habit.

*Plant height.*—18-20.0 cm.

*Plant height (inflorescence included).*—28-33.0 cm.

*Plant width.*—26-34.0 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Variegation.*—Absent.

*Immature leaf, color upper surface.*—Closest to RHS 139A.

*Immature leaf, lower surface.*—Closest to RHS 137A.

*Mature leaf, color upper surface.*—Between RHS 136A and 137A.

*Mature leaf, color lower surface.*—Closest to RHS 137B.

*Length.*—6-7 cm.

*Width.*—8-9 cm.

*Shape.*—Cordate.

*Base shape.*—Cordate.

*Apex shape.*—Acute.

*Margin.*—Slightly dentate.

*Texture upper side.*—Hirsute.

*Texture lower side.*—Hirsute.

*Leaf zonation color.*—Distinct RHS 187B.

*Color of veins, upper surface.*—RHS 139B becoming indistinct.

*Color of veins, lower surface.*—RHS 138B becoming indistinct.

*Pattern of veining.*—Palmate.

*Petiole color.*—RHS 137C.

*Petiole length.*—5.5-7 cm.

*Diameter of petiole.*—0.2 cm.

*Texture.*—Pilose, hirsute, glandular hairs.

Stem:

*Quantity of branches.*—5-8.

*Color of stem.*—Between RHS 143B and RHS 144A.

*Length of stem.*—12-16.0 cm.

*Diameter.*—0.5 cm.

*Length of internodes.*—0.5-2 cm.

*Texture.*—Sparsely hirsute, pilose, glandular hairs.

Peduncle:

*Color of peduncle.*—RHS 143C, coloring with anthocyanins towards close to RHS 181A.

*Length of peduncle.*—11-13.5 cm.

*Peduncle diameter.*—0.3-0.5 cm.

*Texture.*—Hirsute, glandular hairs.

Pedicel:

*Color of pedicel.*—RHS 187B.

*Length of pedicel.*—1.5-2 cm.

*Diameter of pedicel.*—0.15-0.2 cm.

*Texture.*—Sparsely pilose, glandular hiars.

Bud (just before opening):

*Color.*—Closest to RHS 44B.

*Length.*—1.5 cm.

*Width.*—0.8-1.0 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—4-6, with 4-6 immature umbels in various stages.

*Fragrance.*—None.

*Umbel diameter.*—8-9 cm.

*Umbel depth.*—5.5-6.5 cm.

Corolla:

*Form.*—Semi-double.

*Number of petals.*—7-10.

*Diameter of flower.*—3.5-4.5 cm.

*Depth of flower.*—1.5-2 cm.

*Color upper petals, upper surface.*—RHS N30A, lower half of with venation RHS 46A.

*Color upper petals, lower surface.*—RHS N33B, lower half of with venation RHS 46A.

*Length of upper petals.*—2.5 cm.

*Width of upper petals.*—1-2 cm.

*Color lower petals, upper surface.*—RHS N30A.

*Color lower petals, lower surface.*—Rim is RHS 40B, fading to RHS 39C on the lower half, with venation RHS 40B.

*Length of lower petals.*—2.0-2.2 cm.

*Width of lower petals.*—1.4-1.9 cm, petaloids variably smaller smaller and with variable shape.

*Petal shape.*—Obovate to spathulate.

*Apex shape.*—Rounded.

*Margin.*—Entire.

*Base.*—Attenuate.

*Petal texture.*—Papillose on both surfaces.

Calyx:

*Number of sepals.*—5.

*Color of sepals.*—RHS 146B mottled with anthocyanins of about RHS 178B.

*Length of sepals.*—1-1.3 cm.

*Width of sepals.*—0.2-0.4 cm.

*Sepal shape.*—Lanceolate to linear.

*Apex shape.*—Acute.

*Margins.*—Mostly fused.

*Texture, upper surface.*—Glabrous.

*Lower surface.*—Glandular hairs, hirsute.

Reproductive organs:

Gynoecium:

*Pistil.*—1.

*Length.*—0.8 cm.

*Style color.*—Closest to RHS 53A.

*Style length.*—0.5-0.7 cm.

*Stigma color.*—Closest to RHS 53A.

*Ovary color.*—RHS 178B.

*Ovary length.*—0.4-0.5 cm.
*Ovary diameter.*—0.2 cm.
Androecium:
*Number of stamens.*—5-7 with 1-6 staminoids.
*Color of filaments.*—RHS N42A with RHS N155C basally.
*Length filaments.*—0.7-0.8 cm.
*Anther color.*—RHS 48B.
*Length of anthers.*—0.3-0.4 cm.
*Color of pollen.*—Close to RHS173B.
*Pollen amount.*—Abundant.
*Fertility/seed set.*—Has not been determined to date.
*Disease/pest resistance.*—Has not been determined to date.

What is claimed is:

1. A new and distinct variety of *Pelargonium* plant named 'PEQZ0077' substantially as illustrated and described herein.

* * * * *